United States Patent [19]

Karger et al.

[11] Patent Number: 5,089,106

[45] Date of Patent: Feb. 18, 1992

[54] HIGH PERFORMANCE CAPILLARY GEL ELECTROPHORESIS

[75] Inventors: Barry L. Karger, Newton; Roger W. Giese, Quincy; Eva Szoko, Malden, all of Mass.

[73] Assignee: Northeastern University, Boston, Mass.

[21] Appl. No.: 649,673

[22] Filed: Feb. 1, 1991

Related U.S. Application Data

[63] Continuation-in-part of Ser. No. 406,080, Sep. 9, 1989, which is a continuation-in-part of Ser. No. 359,728, May 31, 1989, which is a continuation of Ser. No. 921,311, Oct. 21, 1986, Pat. No. 4,865,706.

[51] Int. Cl.$^5$ .................... G01N 27/26; B01D 57/02
[52] U.S. Cl. .............................. 204/299 R; 204/180.1
[58] Field of Search ............... 204/299 R, 180.1, 183.3

[56] References Cited

U.S. PATENT DOCUMENTS

| | | | |
|---|---|---|---|
| 3,879,204 | 4/1975 | Gervay | 96/83 |
| 4,072,528 | 2/1978 | Bratt | 96/87 R |
| 4,284,518 | 8/1981 | Reick | 252/16 |
| 4,426,489 | 1/1984 | Wessling et al. | 524/815 |
| 4,525,526 | 1/1985 | Wessling et al. | 524/815 |
| 4,680,201 | 7/1987 | Hjerten | 427/230 |
| 4,685,706 | 9/1989 | Karger et al. | 264/182.8 |
| 4,690,749 | 9/1987 | Van Alstine et al. | 204/299 R |
| 4,724,126 | 2/1988 | Dinbergs et al. | 422/131 |
| 4,770,906 | 9/1988 | Harwell et al. | 427/212 |
| 4,791,063 | 12/1988 | Hou et al. | 435/243 |
| 4,900,627 | 2/1990 | Harwell et al. | 428/403 |
| 4,931,328 | 6/1990 | Swedberg | 204/299 R X |
| 4,973,359 | 11/1990 | Yamasoe | 106/14.13 |
| 4,981,882 | 1/1991 | Smith et al. | 523/205 |
| 4,997,536 | 3/1991 | Ohms et al. | 204/180.1 |
| 5,006,313 | 4/1991 | Swedberg | 204/299 R X |
| 5,015,350 | 5/1991 | Wiktorowicz | 204/180.1 |

OTHER PUBLICATIONS

J. K. Towns et al., "Capillary Electrophoretic Separations of Proteins Using Nonionic Surfactant Coatings", Analytical Chemistry, vol. 63, No. 11 (1991), 1126–1132.

Werner G. Kuhr, "Capillary Electrophoresis", Analytical Chemistry, 62 (1990), 403R–414R.

C. J. Van Oss et al., "Cell Microelectrophoresis Simplified by the Reduction and Uniformization of the Electroosmotic Backflow", Analytical Biochemistry, 60 (1974), 242–251.

F. M. Everaerts et al., "Methods for On-Line Determination and Control of Electroendosmosis in Capillary Electrochromatography and Electrophoresis", Journal of Chromatography, 470 (1989) 89–93.

H. Poppe et al., "Capillary Zone Electrophoretic Separations of Proteins in Polyethylene Glycol-Modified Capillaries", Journal of Chromatography, 471 (1989), 429–436.

(List continued on next page.)

Primary Examiner—John Niebling
Assistant Examiner—John S. Starsiak, Jr.
Attorney, Agent, or Firm—Weingarten, Schurgin, Gagnebin & Hayes

[57] ABSTRACT

An improved, highly stable capillary column used in high performance capillary electrophoresis and method of preparing the same. The improved capillary column can significantly reduce the effects of electroosmosis during electrophoresis, is stable for reuse, and enables operation of the capillary column in high electric fields, resulting in high resolution separations in a minimum amount of time. The improved column comprises a capillary having a highly stable, coating matrix on the inner surface of the capillary wall. The highly stable coating matrix includes an intermediate layer hydrophobic phase chemically bonded to the inner wall of the capillary, a detergent which is physically adsorbed to the hydrophobic phase, and a polymerized monomer which is covalently bonded to the adsorbed detergent thereby forming a hydrophilic outer layer of the coating matrix.

18 Claims, 3 Drawing Sheets

OTHER PUBLICATIONS

Stellan Hjerten, "High-Performance Electrophoresis: Elimination of Electroendosmosis and Solute Adsorption", Journal of Chromatography 347 (1985), 191-198.

Kelly A. Cobb, Vladislav Dolnik and Milos Novotny, "Electrophoretic Separations of Proteins in Capillaries with Hydrolytically Stable Surface Structures", Analytical Chemistry, vol. 62, No. 22 (Nov. 15, 1990), 2478-2483.

P. E. M. Verheggen, A. C. Schoots, & F. M. Everaerts, "Feasibility of Capillary Zone Electrophoresis with Suppression of Electroendosmotic Flow in Completely Closed Systems", Journal of Chromatography, 503 (1990) 245-255.

Mark Strege and Avinash Lagu, "Separation of DNA Restriction Fragments by Capillary Electrophoresis Using Coated Fused Silica Capillaries", Analytical Chemistry, vol. 63, No. 13 (Jul. 1, 1991), 1233-1236.

E. S. Huyser, "Free Radical Chain Reactions", Wiley-Interscience, pp. 154-156, N.Y. (1970).

G. Mino and S. Kaizerman, J. Polymer Sci XXXI, pp. 242-243 (1958).

E. Merk Catalog, Oct. 1989.

J. M. Neugebauer, [18] *Detergents: An Overview*, Methods in Enzymology, vol. 182 (1990), pp. 239-253.

M. F. Borgerding and W. L. Hinze and L. D. Stafford, GW Fulp, W. C. Hamlin, *Investigations of Stationary Phase Modification by the Mobile Phase Surfactant in Micellar Liquid Chromatography*, Analytical Chem. vol. 61, No. 13 (Jul. 1, 1989).

W. D. Pfeffer and Edward S. Young, *Open-Tubular Liquid Chromatography with Surfactant-Enhanced Electroosmotic Flow*, Analytical Chem., vol. 62, No. 20 (Oct. 15, 1990).

D. E. Keller, J. L. Torres, R. G. Carbonell, and P. K. Kilpatric, Reversible Conversion of Octadecyl-Bonded Silica to Ion-Exchange Surfaces for Protein Separations, Analytical BioChem, 176, 191-198 (1989).

J. L. Torres, R. Guzman, R. G. Carbonell, and P. K. Kilpatrick, *Affinity Surfactants as Reversibly Bound Ligands for High-Performance Affinity Chromatography*, Analytical BioChem 171, 441-418 (1988).

W. Muller, Eur. J. Biochem. 155 (1986), pp. 213-222.

HIGH PERFORMANCE CAPILLARY GEL ELECTROPHORESIS

CROSS REFERENCE TO RELATED APPLICATIONS

This is a continuation-in-part of application Ser. No. 07/406,080, filed Sept. 9, 1989 which is hereby incorporated by reference. Application Ser. No. 07/406,080 is a continuation-in-part of application Ser. No. 07/359,728, filed May 31, 1989, which is a continuation of parent application Ser. No. 06/921,311, filed Oct. 21, 1986, now U.S. Pat. No. 4,865,706.

A related application is application Ser. No. 07/421,609 filed on Oct. 13, 1989, which is another continuation-in-part application of application Ser. No. 07/359,728.

FIELD OF THE INVENTION

This invention relates to electrophoresis, and more particularly, to improved capillary columns for high performance analytical electrophoresis.

BACKGROUND OF THE INVENTION

High performance capillary gel-electrophoresis has proven to be a powerful technique in the separation of oligonucleotides and medium to high molecular weight polypeptides and proteins as discussed in U.S. Pat. Nos. 4,865,706, 4,865,707, and U.S. pat. app. Ser. No. 07/406,080 hereby incorporated by reference. This technique substantially out-performs more traditional methods of electrophoretic separations such as those conducted on flat plates or slabs.

One important consideration of related to electrophoresis in a capillary is the elimination of electroosmotic flow. A capillary is particularly sensitive to the effects of electroosmotic fluid flow which decreases the resolution of some electrophoretic separations.

In the past, researchers in the field have attempted to control electroosmotic flow and other surface zeta potential associated electrophoretic phenomena by coating the internal surfaces of the electrophoresis tube with various materials to eliminate the characteristic charges associated with those surfaces. For example, in U.S. Pat. No. 3,728,145, Hjerten discloses a method for coating the inner wall of a large bore tube with a neutral hydrophilic substance such as methyl cellulose or polyacrylamide to reduce electroosmosis in free-zone electrophoresis in open tubes. In a later patent, U.S. Pat. No. 4,860,201, Hjerten discloses a method for coating the inner wall of a narrow bore capillary with a monomolecular coating of polyacrylamide bonded to the capillary wall by means of a bifunctional reagent. These capillaries are also open tubes to be used for free-zone electrophoresis. In the background of the '201 patent, it is stated that coating the inner wall of the electrophoresis tube with a polymeric substance to reduce adsorption and electroosmosis suffers from the drawbacks that the coating material must be renewed frequently since it apparently flushes out of the capillary during use, and that relatively thick layers necessary for complete coating cause zone deformation in electrophoresis. This '201 patent thus teaches away from coating the wall of a capillary with a polymeric substance applied as an adsorbed layer, and discloses instead that for suppression of electroosmosis, a monomolecular layer of polyacrylamide should be covalently attached to the wall.

The small amount of work in the field of gel electrophoresis in capillaries by researchers other than the present inventors has generally resulted in columns which were not highly stable and could not be subjected to sufficiently high electric fields to achieve high efficiencies and high resolution separations.

The inventors have previously addressed the need for an improved coating to reduce the problem of electroosmotic flow in a gel-filled capillary in application Ser. No. 07/406,080. This application discloses a capillary column for high performance gel electrophoresis which includes a thin layer of coating material covalently bonded to the inner surface of the capillary wall, and a thin layer of a hydrophilic polymer adsorbed on the layer of coating material. It was found that the layer of hydrophilic polymer is highly stable, effectively reduces electroosmosis, stabilizes the column, and unexpectedly, enables operation of the capillary column in high electric fields (or more exactly, high power), resulting in high resolution separations.

The inventors have since found that high performance electrophoresis in a capillary can be even more powerful if the effects of electroosmosis in the capillary column can be further controlled, and if the capillary column itself is highly stable and capable of being re-used numerous times.

Criteria such as those just described requires a capillary column in which the effects of electroosmosis can be made almost negligible, and which is highly stable so as to withstand repeated use in high electric fields and repeated washings.

SUMMARY OF THE INVENTION

The above-identified need for an improved, highly stable capillary electrophoresis column in which the effects of electroosmosis can be controlled, e.g., significantly reduced, during electrophoresis is answered by the present invention, which provides an improved capillary for high performance electrophoresis. It includes a capillary having a highly stable coating matrix on the inner surface of the capillary wall. The highly stable coating matrix includes an intermediate layer hydrophobic phase chemically bonded to the inner wall of the capillary, a detergent which is physically adsorbed to the hydrophobic phase, and a monomer which becomes covalently bonded to the adsorbed detergent upon polymerization of the monomer thereby forming a hydrophilic outer layer of the coating matrix.

The hydrophobic phase of the coating matrix is generally made using a reagent possessing reactive functional groups capable of reacting with reactive functionalities on the interior surface of the capillary wall, silanol groups, for example. The remainder of the reagent is a hydrophobic moiety such as a straight-chain, branched, aromatic, cyclic, or substituted hydrocarbon including combinations of these moieties.

The detergent which is adsorbed to the intermediate layer hydrophobic phase may be ionic, zwitterionic, or nonionic, and possesses a hydrophilic head group capable of forming covalent bonds with monomers brought in contact with the detergent coating upon polymerization of the monomers.

The above described matrix unexpectedly provides an extremely stable, polar coating matrix having a hydrophilic outer layer on the inner wall of the capillary which does not readily break down and flush out of the capillary during use as has been a major problem with capillary coatings in the past. Furthermore, the coating matrix can significantly reduce electroosmosis, and other surface zeta potential associated electrophoretic phenomena, and enables operation of the capillary column in high electric fields (or more exactly, high power density), resulting in high resolution separations. Moreover, the coating matrix remains stable and intact after multiple washings as well as after having polymeric gel filling pushed out and replaced for repeated use of the capillary column.

The improved capillary of the invention is prepared as follows: first the interior surface of the capillary is contacted with one or both of a basic and an acidic material to activate it, then it is treated with a solution of appropriate hydrophobic reagent capable of chemically bonding to the capillary wall and forming a hydrophobic phase. Then, a detergent is adsorbed onto the hydrophobic phase. Next, the detergent-coated capillary wall is exposed to a monomer capable of undergoing a free radical polymerization reaction. The monomer may optionally include a crosslinker. An initiator and catalyst are added to cause the free radical polymerization of the monomers and any crosslinking agent, and covalent attachment between the monomers and the adsorbed detergent. After polymerization at the wall of the capillary is complete, residual polymerized material not bound to the adsorbed detergent is blown or sucked out of the capillary. The bore of the capillary may then be filled with a solution containing at least one monomer, and optionally at least one crosslinking agent, plus at least one free radical source and an appropriate catalyst, and this mixture is allowed to polymerize in the tube, ultimately forming a polymeric matrix which fills the capillary bore.

The capillaries of the invention are unusually stable and function well under applied electric fields typically of 300 volts/cm or higher, and with currents typically up to approximately 30 microamperes or above. Under these conditions, extremely high resolution separations are obtained on very small amounts of material. In addition, the capillaries of the invention have been demonstrated to resolve mixtures of DNA fragments as a linear function of the logarithm of their molecular weights. Accordingly, they permit convenient and accurate molecular weight determinations on nanogram or lower amounts of unknown biopolymers.

The coating matrix of the invention can also be used to form a highly stable, hydrophillic coating matrix on the internal and external surfaces of alkyl-bonded, porous silica particles used for high performance liquid chromatography (HPLC). It can be also used on porous, hydrophobic HPLC particles containing polystyrene or other organic polymers.

DETAILED DESCRIPTION OF THE INVENTION

Figure 1:
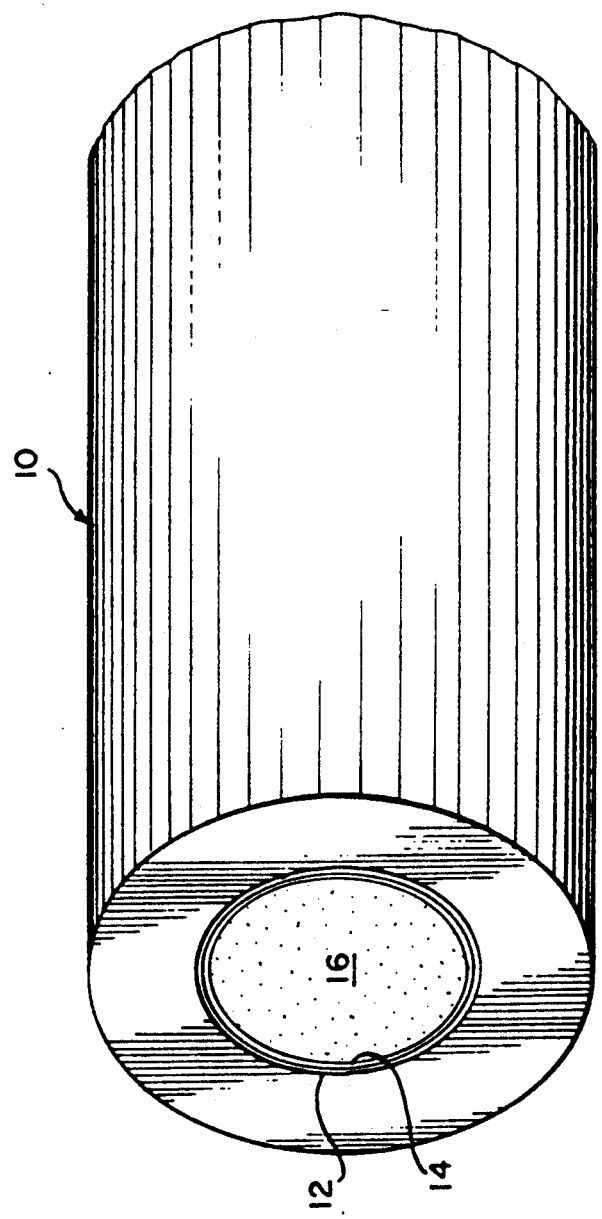
FIG. 1 shows a magnified perspective view of the end of the gel-containing capillary of the invention.

As shown in FIG. 1, the capillary column of the invention includes a capillary 10, having a highly stable, coating matrix 12 which includes a hydrophilic outer layer on the inner surface 14 of the capillary wall. The capillary of the invention may also include a polymeric gel filling 16 located within the bore of the capillary 10.

As employed herein, the term polymeric gel means a three-dimensional network of polymer chains held together by any of a variety of means such as covalently bonded crosslinking units, van der Waals attractive forces, hydrogen bonds, entanglement of the molecular chains, etc., and dispersed in a liquid phase. The polymeric network provides sufficient structure for a degree of rigidity, and other components of the system occupy the spaces between the polymeric chains.

The capillary may be made of any of a variety of materials provided that the detection system to be employed in the electrophoresis can function adequately with the particular material employed. Preferably, the capillary is made of fused silica and, for exemplary purposes, an improved capillary column of fused silica will be described in detail.

The capillary dimensions are important because, for a given electric field, as the internal diameter of the capillary is reduced, the electric current and the resultant heating produced by a particular applied electric field is reduced. Thus, for highest resolution separations it is desirable that the capillary have a minimum internal diameter. With the improved capillaries of this invention, however, this factor is somewhat less important than formerly. Accordingly, capillaries having internal diameters in the range between 10 and 2000 micrometers function in the invention. A preferred range of internal diameters is 10 to 200 micrometers. A polyimide coating on the outer surface of the capillary permits easy handling of thin-walled capillaries.

The highly stable coating matrix 12 between the polymeric gel 16 and the inner surface 14 of the capillary wall includes an intermediate layer hydrophobic phase chemically bonded to the inner wall of the capillary, a detergent which is physically adsorbed to the hydrophobic phase, and a monomer which becomes covalently bonded to the adsorbed detergent upon polymerization of the monomer thereby forming a hydrophilic outer layer of the coating matrix.

The hydrophobic phase is generally made using a reagent possessing one or more reactive functional groups capable of reacting with reactive functionalities on the interior surface of the capillary wall, silanol groups, for example. The remainder of the reagent is a hydrophobic moiety such as a straight-chain, branched, aromatic, cyclic, or substituted hydrocarbon including combinations of these moieties.

A preferred intermediate layer hydrophobic phase for use with fused silica capillaries is made using a hydrophobic reactive silane which is capable of chemically bonding to the fused silica wall of the capillary. Examples of reactive silanes suitable for chemically bonding the hydrophobic phase to the capillary wall include alkyltrialkoxysilane, alkyltrichlorosilane, and alkyl di- or tri- ethoxy or methoxy silanes. A preferred hydrocarbon moiety is n-octadecyl ($C_{18}$), although other hydrocarbon chains of $C_7$-$C_{30}$ carbons are suitable as well.

The detergent which is physically adsorbed to the hydrophobic phase may be ionic, zwitterionic, or nonionic. A nonionic detergent is preferred for low electroosmotic flow. A suitable detergent possesses the following structural formula:

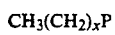

or

where x is a number between 8 and 40 is a hydrophilic moiety possessing one or more of the following groups:

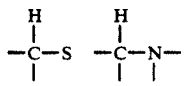

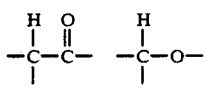

P preferably is a hydrophilic moiety possessing three or more hydroxyl groups, such as a carbohydrate group, for low electroosmotic flow.

A preferred detergent is an alkyl maltoside such as n-dodecyl-B-D-maltoside. Other possible ionic, zwitterionic, and nonionic detergents include, but are not limited to, alkyl polyethylene detergents (e.g., Brij, Triton X and Tween detergents), n-dodecylamine, alkyl carboxylate, lysolecithin, and steroid detergents (e.g., sodium cholate and Big CHAP). Other polyhydroxy detergents such as n-dodecylsucrose can be used as well. Further details regarding the adsorption of detergents is available (e.g., J. M. Neugebauer, "Detergents: An Overview," Meth. in Enzymol. 182, 1990, pp. 239-253).

Suitable choices for a monomer to which the adsorbed detergent coating is exposed, and to which the detergent subsequently becomes covalently attached upon polymerization of the monomer include olefinic monomers such as vinyl monomers, acrylyl monomers, acrylamide, acrylic acid, methyl acrylamide, and N,N,N-tris(hydroxymethyl) acrylamide. Other monomers include but are not limited to trimethylaminoethylacrylamide, diethylaminoethylacrylamide, dimethylaminoethylacrylamide and 2-sulfonyl, 1,1-dimethylethylacrylamide. Optionally, the monomer may also include a crosslinking agent such as N,N'-methylenebisacrylamide.

The details of the chemistry of the covalent attachment of polymerized monomers to detergents are known in the art. For example, it is known that moieties like

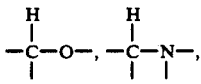

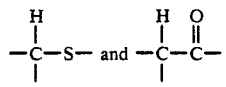

can be reacted with free radical initiators to form corresponding free radicals

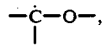

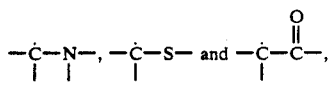

respectively, that, in turn initiate polymerization reactions of olefinic monomers, especially vinyl monomers such as acrylic acid (E. S. Huyser, "Free Radical Chain Reactions", Wiley-Interscience, New York, 1970, pp. 154-156). This type of reaction has been used for example, to graft vinyl monomers such as acrylamide, acrylonitrile and methyl acrylate onto hydroxylic polymers such as polyvinyl alcohol, dextrans, starches and carrageenans (G. Mino and S. Kaizerman, J. Polymer Sci. XXXI, 1958, pp. 242-243). N-Substituted acrylamides $CH_2$=CHCONHR, where R=$CH_2CH_2N^+(CH_3)_3$(trimethylaminoethylacrylamide), R=$CH_2CH_2N(CH_2CH_3)_2$ (diethylaminoethylacrylamide), R=$CH_2CH_2N(CH_3)_2$ (dimethylaminoethylacrylamide), and R=$C(CH_3)_2CH_2SO_3^-$ (2-sulfonyl, 1,1-dimethylethylacryl-amide), and also acrylic acid, have been similarly grafted to porous diol-silica and Fractogel TSK chromatographic packings (E. Merck Catalog, October, 1989; W. Muller, Eur. J. Biochem. 155, 1986, pp. 213-222).

If a polymeric gel filling 16 is to be employed, the polymeric gel material employed can be any polymer which has a pore structure which can be varied. It may or may not be crosslinked. Examples of suitable polymeric systems are polyacrylamide, agarose, and mixtures of agarose and polyacrylamide. Suitable crosslinking agents are N,N'-methylenebisacrylamide, N,N'-diallyltartardiamide, and N,N'-cystamine-bisacrylamide. Still other monomers and crosslinkers will suggest themselves to those skilled in the art.

The polymerization reaction is preferably initiated with ammonium persulfate and N,N,N',N'-tetramethyleneethylenediamine (TEMED), though other free radical polymerization initiators may be employed, as known by those skilled in the art.

The improved capillaries of the invention are generally prepared as follows.

First, the inner surface of the capillary is coated with a highly stable coating matrix. The coating is prepared by first, activating the interior surface of the capillary by bringing it into contact with an acidic and/or basic solution such as a 1M KOH solution for 1 hour then a 1M HCl solution for 1 hour at room temperature. The capillary is then washed with distilled water until its interior becomes neutral and dried at temperatures ranging between 95° C.-125° C. for at least 10 hours to overnight. All of these solutions are flushed from the capillary using a stream of inert gas such as $N_2$.

The time and temperature employed in activating the capillary are selected such that they are sufficient to activate the capillary so that good bonding between the capillary and the hydrophobic phase is achieved.

The activated capillary is then flushed with about 300 column volumes of a solution containing the intermediate layer hydrophobic phase of the coating matrix such as a hydrophobic silane in a suitable solvent. A suitable hydrophobic silane in a solvent includes, but is not limited to, 1% octadecyltriethoxysilane in toluene containing 0.04% triethylamine. The column is then washed with toluene and purged with $N_2(g)$. The column is then heated to a temperature of about 100° C. at least 2 hours. Finally the column is washed with solvent such as toluene and purged with inert gas such as $N_2(g)$.

To insure that all of the activated groups on the interior of the capillary have been reacted, the capillary is flushed with a solution of endcapping reagent such as trimethylchlorosilane in toluene for 10 minutes. The endcapping reagent will react and neutralize exposed unreacted silanol groups on the wall of a fused silica capillary. The capillary is then washed with solvent such as toluene, and purged with an inert gas such as $N_2$. The capillary is then heated in an oven at a temperature of about 100° C. for at least 30 minutes and then washed with solvent such as toluene and/or methanol and/or water.

Next, a detergent is adsorbed onto the hydrophobic phase. A solution containing a suitable detergent such as a 10% solution dodecylmaltoside in water is streamed through the capillary for about 1 hour (300 column volumes). The capillary is then purged with an inert gas such as $N_2$.

The inner wall of the capillary which is now coated with detergent is flushed with a solution containing a monomer such as 3% acrylamide, and also containing a polymerization catalyst such as ammonium persulfate and TEMED. A crosslinking reagent such as N,N'-bis(-methyleneacrylamide) may also be present in a concentration of 0.3%. The monomer along with any crosslinking reagent is allowed to polymerize for at least 1 hour and the residual polymerized material not bound to adsorbed detergent is then blown ($N_2(g)$) or sucked out of the capillary. The capillary is washed with 1000 column volumes of water. The polymerization is then repeated and the residual polymerized monomer not bound to the adsorbed detergent is again pushed out, and the column is washed as before with water.

After the coating matrix is prepared on the interior of the capillary, the capillary may optionally be filled with a polymeric gel filling. The preparation of a crosslinked or uncrosslinked polymeric gel filling in a capillary is known in the art and described in detail in application Ser. No. 07/406,080.

After its preparation, the capillary column of the invention is ready for repeated use in experiments requiring electrophoretic separation of analytes. In employing the capillary column of the invention in electrophoresis, apparatus and techniques are known to those skilled in the art and are described in detail in application Ser. No. 07/406,080.

The improved capillary columns of the invention which contain an improved coating matrix are extremely versatile and eliminate the effects of electroosmosis and other surface zeta potential electrophoresis associated phenomena under a variety of electrophoretic conditions. The exceptional stability of the coating matrix enables the column to withstand repeated uses including having an polymeric gel filling pushed out of the column and replaced numerous times without the need for reapplying the coating. The coating further stabilizes the column under relatively harsh electrophoretic conditions such as high temperatures and weak buffers. Most importantly, the improved capillary columns of the invention can be operated in high electric fields (or at high power), without the breakdown of the coating and changes in the effects of electroosmosis as has been a major problem in the past. Therefore, the columns of the invention permit high resolution separations to be achieved in a short period of time.

The coating matrix of the invention can also be used to form a highly stable, hydrophilic coating matrix on the internal and external surfaces of alkyl-bonded, porous silica particles used for high performance liquid chromatography (HPLC). It can also be used on porous HPLC particles containing polystyrene.

The following experimental section is intended as exemplary of the invention, and are not intended to limit or define the scope of the invention.

EXPERIMENTAL SECTION

The Effects of Electroosmotic Flow in the Capillary Columns of the Invention as Compared to Other Capillary Columns As discussed above, the highly stable coating matrix of the capillary columns of the invention can significantly reduce the effects of electroosmosis as compared to other capillaries which do not possess the superior coating. A test which measures the electroosmotic flow ($cm^2 V^{-1} S^{-1}$) in a column is described in detail in a paper by X. Huang, M. F. Gordon and R. N. Zare: Anal. Chem. 60 1837-1838 (1988) hereby incorporated by reference. In this test, the columns are each placed in an electrophoretic apparatus so that each end of the column is immersed in a solution of "running" buffer. An electric field is applied across the column and the current is measured. The electroosmotic flow can be measured as a linear function of the change in current which occurs as the concentration of the buffer solution (pH7) is changed. In this experiment, a capillary column of the invention having a coating of polyacrylamide covalently attached to a detergent, dodecylmaltoside, the detergent being physically adsorbed to an alkylsilane which in turn is covalently attached to the wall of the column, is compared to a fused silica capillary column which is uncoated, and also to a fused silica capillary column which has a detergent coating of dodecylmaltoside adsorbed onto an alkylsilane which is covalently attached to the capillary column. The results of the experiment are found in Table I below.

TABLE 1

| | ELECTROOSMOTIC FLOW ($cm^2 V^{-1} S^{-1}$) Measured at pH 7.0 | | |
|---|---|---|---|
| Capillaries Tested | pH 7 buffer | Methanol | pH 7.0 buffer comprising 0.2M NaCl at 50° C. |
| Uncoated Fused Silica | $3.2 \times 10^{-4}$ | — | — |
| Alkylsilane/ dodecylmaltoside coated | $0.56 \times 10^{-4}$ | — | — |
| Alkylsilane/ dodecylmaltoside/ | non-measurable | non-measurable | non-measurable |

TABLE 1-continued

ELECTROOSMOTIC FLOW ($cm^2 V^{-1} S^{-1}$)
Measured at pH 7.0

| Capillaries Tested | pH 7 buffer | Methanol | pH 7.0 buffer comprising 0.2M NaCl at 50° C. |
|---|---|---|---|
| acrylamide coated | | | |

Method used: X. Huang, M. F. Gordon and R. N. Zare: Anal. Chem. 60 1837-1838 (1988).

This data shows that electroosmotic flow in a column of the invention is negligible. The data further indicates that the electroosmotic flow remains negligible even when the buffer used is methanol, or is a buffer containing 0.2M NaCl at a temperature of 50° C. Therefore, the capillary column of the present invention not only renders the effects of electroosmosis negligible under normal conditions, but is highly stable and continues to eliminate the effects of electroosmosis even at temperatures as high as 50° C.

By contrast, the uncoated fused silica column and the column coated with a hydrophobic material and adsorbed detergent with no covalent attachment of acrylamide, showed significantly higher measurements of electroosmotic flow as compared to the column of the invention.

Testing of the Columns of the Invention

A fused silica capillary was coated with the highly stable coating matrix as was previously described. The coating comprised a hydrophobic phase of $C_{18}$-alkylsilane covalently attached to the fused silica wall, a detergent, dodecylmaltoside, physically adsorbed to the hydrophobic phase and polymerized acrylamide monomer covalently attached to the detergent coating. The column was filled with a polymeric gel filling comprising 3% total monomer and 0% crosslinker.

A sample of $\phi$X174 RF DNA-HaeIII digest was prepared for electrophoresis in the standard manner known in the art, and an aliquot of the sample was injected into the column by application of an electrical field of 100 volts/cm for 15 seconds. Electrophoresis was conducted at 25° C. in a 0.1M TBE buffer having a pH of 8.3 at 200 V/cm and a current of 10 mA over the 20 cm migration distance. The results are shown in the electropherogram in FIG. 2.

After the run was complete, the polymeric gel filling was pushed out of the column, and a new polymeric gel filling comprising 3% total monomer and 0% crosslinker was replaced in the column without renewing the coating matrix.

Electrophoresis was conducted again using a sample of pBr322 DNA-Hae III digest at 50° C. and 300 v/cm, 25° C. and 100 v/cm higher than the previous run. The results are shown in FIG. 3.

Figure 2:
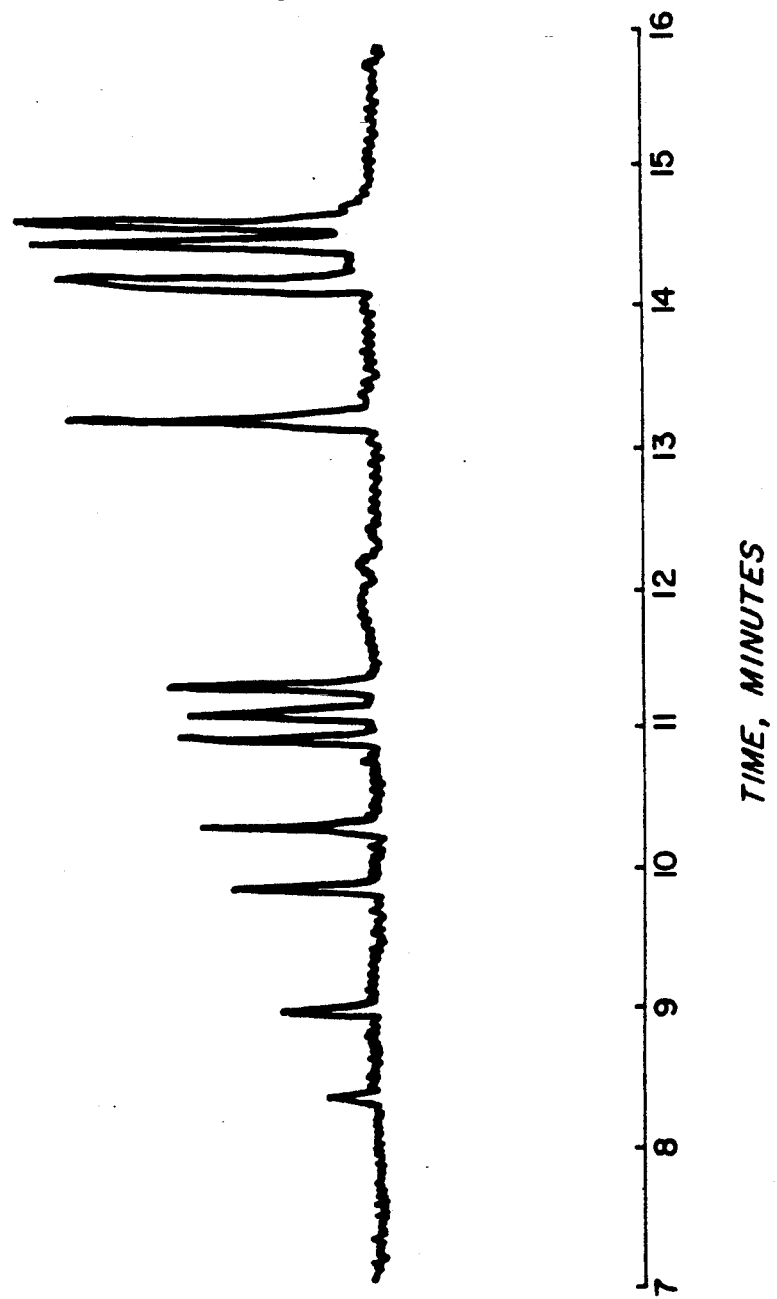
FIG. 2 is an electropherogram showing the electrophoretic separation of $\phi$X174 RF DNA-Hae III digest on a capillary column of the invention containing a polymeric gel filling which is 3.0% total monomer and 0% crosslinker. The pH of the 0.1 M TBE buffer was 8.3, and electrophoresis was conducted at 25° C. in an applied field of 200 volts/cm over a 20 cm migration distance.
Figure 3:
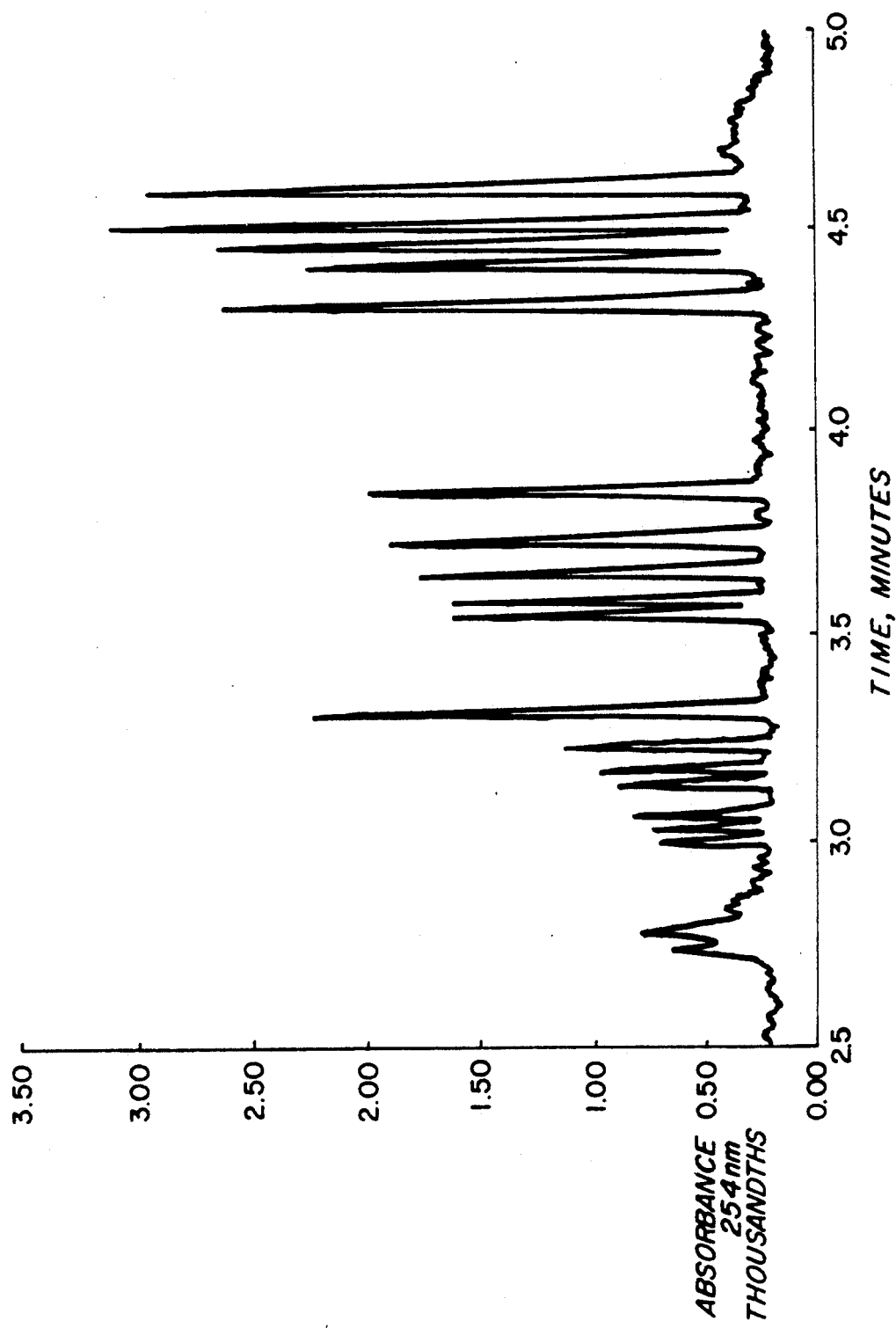
FIG. 3 is an electropherogram of an electrophoretic separation of pBr322 RF DNA-Hae III digest on a capillary column of the invention. The electrophoretic conditions were the same as those employed in the separation shown in FIG. 2 except the applied field was 300 volts/cm and temperature was 50° C.

The data shown in FIGS. 2 and 3 indicate that the capillary columns of the invention permit extremely high resolution due in part to the suppression of electroosmosis by the highly stable coating matrix. Moreover, the columns are stable enough to have the uncrosslinked gel pushed out and refilled without effecting the resolution of the DNA sample in a subsequent run as is clearly shown from the electropherogram of FIG. 3.

Other embodiments of the invention will be apparent to those skilled in the art from a consideration of this specification or practice of the invention as disclosed herein. It is intended that the specification and examples be considered as exemplary only, with the true scope and spirit of the invention being indicated by the following claims.

What is claimed is:

1. An improved, highly stable capillary column for high performance capillary electrophoresis comprising:
    a capillary having an interior cavity and a wall with an inner surface;
    a highly stable coating matrix on said inner surface of said wall, said coating matrix comprising:
    an intermediate layer hydrophobic phase covalently bonded to said inner surface of said wall;
    a detergent physically adsorbed to said hydrophobic phase; and
    a polymerized monomer covalently attached to said detergent thereby forming a hydrophilic outer layer of said coating matrix.

2. The capillary of claim 1 further comprising a polymeric gel filling in said interior cavity.

3. The capillary of claim 1 wherein said capillary is made of fused silica.

4. The capillary of claim 1 wherein said hydrophobic phase comprises alkylsilane moieties.

5. The capillary of claim 4 wherein said hydrophobic phase comprises $C_{18}$-silane moieties.

6. The capillary of claim 1 wherein said detergent is selected from the group consisting of steroid detergents, -polyoxyethylene detergents, polyhydroxy detergents, -amines, and -carboxylates.

7. The capillary of claim 1 wherein said detergent is dodecylmaltoside.

8. The capillary of claim 1 wherein said monomer is an olefinic monomer selected from the group consisting of vinyl monomers, acrylyl monomers, acrylamide, and N,N,N-tris(hydroxymethyl) acrylamide.

9. The capillary of claim 1 wherein said polymerized monomer further includes at least one crosslinking agent.

10. The capillary of claim 2 wherein said polymeric gel comprises polymerized uncrosslinked monomer.

11. The capillary of claim 2 wherein said polymeric gel comprises at least one polymerized monomer and at least one crosslinking agent.

12. A method of preparing a highly stable capillary column for high performance capillary electrophoresis comprising the steps of:
    providing a fused silica capillary column having an interior cavity and a wall having an inner surface;
    chemically bonding a hydrophobic phase to said inner surface of said wall;
    physically adsorbing a detergent onto said hydrophobic phase;
    exposing said detergent to a monomer capable of undergoing a free-radical polymerization reaction; and
    polymerizing said monomer to cause covalent bonds to develop between said monomer and said adsorbed detergent.

13. The method of claim 12 further comprising the step of filling said interior cavity with a polymeric gel.

14. A method of performing high performance capillary electrophoresis, comprising:
    injecting an aliquot of a sample containing analytes to be separated into a capillary column comprising:
    a capillary having an interior cavity and a wall with an inner surface;

a coating matrix on said wall of said inner surface, said coating matrix comprising:

a hydrophobic phase covalently bonded to said inner surface of said wall;

a detergent physically adsorbed to said hydrophobic phase; and a polymerized monomer covalently attached to said detergent;

applying an electric field of at least 100 volts/cm; and instrumentally detecting and measuring the separated analytes sequentially.

15. The method of claim 14, wherein said capillary further comprises a polymeric gel filling said interior cavity.

16. An improved coating matrix for the inner surface of fused silica capillaries used in high performance, high precision capillary electrophoresis comprising:

a hydrophobic phase covalently bonded to said inner surface of said fused silica capillary;

a detergent physically adsorbed to said hydrophobic phase; and a polymerized olefinic monomer covalently attached to said detergent.

17. The capillary of claim 1 wherein said monomer is selected from the group consisting of acrylic acid, trimethylamino-ethylacrylamide, diethylaminoethylacrylamide, dimethylaminoethyl-acrylamide and 2-sulfonyl-1,1-dimethylethylacrylamide.

18. The capillary of claim 6 wherein said polyhydroxy detergents are selected from the group consisting of alkyl maltosides, -glucamides, and polyhydroxy steroid detergents.

* * * * *